United States Patent
Shen

(10) Patent No.: US 6,245,325 B1
(45) Date of Patent: Jun. 12, 2001

(54) ENHANCED ANTIPERSPIRANT SALTS STABILIZED WITH CALCIUM AND CONCENTRATED AQUEOUS SOLUTIONS OF SUCH SALTS

(75) Inventor: Yan-Fei Shen, Canton, MA (US)

(73) Assignee: The Gillette Company, Boston, MA (US)

( * ) Notice: Subject to any disclaimer, the term of this patent is extended or adjusted under 35 U.S.C. 154(b) by 0 days.

(21) Appl. No.: 09/435,183

(22) Filed: Nov. 5, 1999

Related U.S. Application Data

(63) Continuation of application No. PCT/US99/17780, filed on Aug. 5, 1999, which is a continuation-in-part of application No. 09/136,823, filed on Aug. 19, 1998, now Pat. No. 6,042,816.

(51) Int. Cl.[7] .................................................. A61K 7/34
(52) U.S. Cl. .............................................. 424/65; 434/68
(58) Field of Search ........................................ 424/65, 68

(56) References Cited

U.S. PATENT DOCUMENTS

| | | | |
|---|---|---|---|
| 2,350,047 | 5/1944 | Kiarmann et al. | 167/90 |
| 2,571,030 | 10/1951 | Govett et al. | 167/90 |
| 3,553,316 | 1/1971 | Rubino | 424/68 |
| 3,979,510 | 9/1976 | Rubino | 424/47 |
| 3,991,176 | 11/1976 | Rubino | 424/47 |
| 3,995,788 | 12/1976 | Rubino | 424/47 |
| 3,996,346 | 12/1976 | Staffer et al. | 424/67 |
| 4,017,599 | 4/1977 | Rubino | 424/47 |
| 4,021,536 | 5/1977 | Rubino | 424/47 |
| 4,526,780 | 7/1985 | Marschner et al. | 424/66 |
| 4,659,560 | 4/1987 | Bews et al. | 424/47 |
| 4,775,528 | 10/1988 | Callaghan et al. | 424/66 |
| 4,859,446 | 8/1989 | Abrutyn et al. | 423/462 |
| 4,944,933 | 7/1990 | Inward | 423/462 |
| 5,162,378 | 11/1992 | Guthauser | 514/785 |
| 5,330,751 | 7/1994 | Curtin et al. | 424/66 |
| 5,346,694 | 9/1994 | Juneja | 424/66 |
| 5,356,609 | 10/1994 | Giovanniello | 423/462 |
| 5,534,246 | 7/1996 | Herb et al. | 424/66 |
| 5,643,558 | 7/1997 | Provancal et al. | 424/66 |
| 5,676,936 | 10/1997 | Park | 424/65 |
| 5,955,065 | 9/1999 | Thong et al. | 424/68 |
| 6,042,816 | * 3/2000 | Shen | 424/65 |

FOREIGN PATENT DOCUMENTS

| | | |
|---|---|---|
| 1068215 | 12/1979 | (CA) . |
| 880261 | 10/1961 | (GB) . |
| 2 048 229 | 12/1980 | (GB) . |
| wo 96/19228 | 6/1996 | (GB) . |

OTHER PUBLICATIONS

Michniak–Mikolajczak, An In Vitro Investigation of the Astringency Property of Certain Anhidrotic Solutions, 1985, 37, 141–145, Pol. J. Pharmacol. Pharm.

Michniak, Studies on the mechanism to topical anhidrosis due to polyvalent cations, 1981, 3, 29–36, International Journal of Cosmetic Science.

* cited by examiner

*Primary Examiner*—Michael A Williamson
(74) *Attorney, Agent, or Firm*—Stephen P. Williams

(57) ABSTRACT

The present invention relates to enhanced efficacy antiperspirant salts containing calcium and an amino acid or a hydroxy acid and particularly to stabilized aqueous solutions of such salts. The present invention also embraces methods of making these antiperspirant salts and solutions and compositions containing same.

27 Claims, No Drawings

ENHANCED ANTIPERSPIRANT SALTS STABILIZED WITH CALCIUM AND CONCENTRATED AQUEOUS SOLUTIONS OF SUCH SALTS

CROSS-REFERENCE TO RELATED APPLICATIONS

This application is a continuation of PCT/US99/17780 filed Aug. 5, 1999, which is a continuation-in-part of U.S. Ser. No. 09/136,823 filed Aug. 19, 1998, now U.S. Pat. No. 6,042,816.

BACKGROUND OF THE INVENTION

The present invention relates to enhanced efficacy antiperspirant salts containing calcium and an amino acid or a hydroxy acid and particularly to stabilized aqueous solutions of such salts. The present invention also embraces methods of making these antiperspirant salts and solutions and compositions containing same.

Enhanced efficacy aluminum and aluminum-zirconium antiperspirant salts are well known and are described, for example, in GB 2,048,229 and U.S. Pat. No. 4,775,528. These salts are generally made by heat treating a relatively dilute solution of the salt (e.g. about 10% by weight) to increase its HPLC peak 4 to peak 3 ratio, then spray drying to a powder. These salts typically have an HPLC peak 4 to peak 3 area ratio of 0.7 or higher, with at least 70% of the aluminum contained in said peaks. However, these enhanced salts are also known to rapidly revert back to their non-enhanced state (for example, as evidenced by an HPLC peak 4 to peak 3 area ratio of 0.3 or less) in aqueous solution, particularly at concentrations greater than 20%. Consequently, the enhanced antiperspirant salts are generally only available in powder form. Moreover, the enhanced salts are generally only formulated into finished formulations as suspended powders in order to retain their enhanced efficacy.

In U.S. Pat. No. 5,330,751, there is disclosed a method of making stable aqueous solutions of enhanced efficacy antiperspirant salts by mixing a relatively low concentration of the salt (5–20%) with monosilicic acid. This method has several disadvantages. It requires relatively low concentrations of the antiperspirant salt and it produces silica as a biproduct, which makes the solution cloudy and is difficult to remove.

In U.S. Pat. No. 5,643,558 there is disclosed a method of preparing a solution of an enhanced efficacy aluminum antiperspirant salt in a polyhydric alcohol by (a) providing an aqueous solution of about 5 to 20% by weight of an enhanced efficacy aluminum antiperspirant salt in water, (b) mixing the aqueous solution with a liquid polyhydric alcohol (e.g. propylene glycol) to provide a mixed solution, and (c) rapidly evaporating the water from the mixed solution under vacuum to provide a liquid polyhydric alcohol solution containing about 20 to 50% enhanced efficacy aluminum antiperspirant salt and about 2 to 16% water, with the balance being said polyhydric alcohol. When an aluminum-zirconium complex is desired in the final product, the zirconium salt can be added at any stage prior to the evaporation step (c). If the water content exceeds 16%, the peak 4 to, 3 ratio of the salt deteriorates on storage.

In U.S. Pat. No. 6,010,688, by the present inventor, there is disclosed a method of stabilizing an aqueous solution of an enhanced efficacy aluminum or aluminum-zirconium antiperspirant salt against rapid degradation of the HPLC peak 4 to peak 3 area ratio of said salt by adding to said aqueous antiperspirant salt solution an effective amount of a polyhydric alcohol having from 3 to 6 carbon atoms and from 3 to 6 hydroxyl groups to form a stabilized aqueous antiperspirant salt solution. A second disclosed method involves preparing an enhanced efficacy aluminum antiperspirant salt by heating an aqueous solution of an aluminum antiperspirant salt in the presence of a polyhydric alcohol having from 3 to 6 carbon atoms and from 3 to 6 hydroxyl groups at a temperature of at least 50° C. for a time sufficient to convert the salt to an enhanced salt. A third disclosed method is an improvement in the method of making an aluminum hydroxy halide or an aluminum hydroxy nitrate by reacting aluminum with an aqueous solution of aluminum halide or aluminum nitrate (or with aqueous hydrogen halide or nitric acid), wherein the improvement comprises including a polyhydric alcohol having from 3 to 6 carbon atoms and from 3 to 6 hydroxyl groups in the reaction mixture. Also disclosed are compositions produced by the foregoing methods. These include compositions comprising, in percent by weight (USP), about 18 to 45% of an enhanced efficacy aluminum or aluminum-zirconium antiperspirant salt, about 20 to 70% water, and about 5 to 60% of a polyhydric alcohol having from 3 to 6 carbon atoms and from 3 to 6 hydroxyl groups. The HPLC peak 4 to peak 3 area ratio of the antiperspirant salt in these compositions does not degrade as quickly or to as low a point as similar compositions without the polyhydric alcohol.

In U.S. Pat. No. 2,571,030 there are disclosed calcium aluminum basic chloride antiperspirant salts which have less of a deteriorating effect on fabric than aluminum basic chloride (chlorhydroxide). These salts are made by reacting calcium carbonate with aluminum chlorhydroxide or with aluminum chloride and aluminum powder, or by adding calcium chloride dihydrate to aluminum chlorhydroxide. This patent suggests that the antiperspirant salts may have 0.2 to 15 parts by weight of calcium for every 100 parts by weight of aluminum. The salts do not contain any amino acid.

In U.S. Pat. No. 3,979,510 there are disclosed aluminum-zirconium antiperspirant compositions containing aluminum buffering agents to raise the pH. The aluminum buffering agents may include well-known antacid complexes such as hydrated magnesium aluminum sulfate as well as the co-precipitates of aluminum hydroxide with magnesium or calcium carbonate. Examples VIII and XI describe the preparation of solid non-enhanced Al-Zr salts containing 0.6% and 0.2% calcium respectively (Ca:Al+Zr weight ratio is 1:45 and 1:114), but neither salt contains an amino acid.

In U.S. Pat. No. 3,998,788 there are disclosed aluminum-zirconium antiperspirant compositions containing trace amounts of alkaline earth metal salts, particularly calcium or magnesium or both, and preferably magnesium. Generally, the compositions will contain one part alkaline earth metal to 30–1000 parts by weight of aluminum plus zirconium. A solution containing 5–15% aluminum plus zirconium (roughly 10 to 30% active) will contain about 0.001–0.1% alkaline earth metal. Although the patent suggests that the Al-Zr compositions may be buffered with a variety of buffering agents, including urea and water soluble amino acids among others, no compositions containing an amino acid are exemplified. In fact, no Al-Zr composition containing calcium is exemplified.

In U.S. Pat. No. 4,021,536 there are disclosed astringent zirconium compositions containing a magnesium salt, such compositions having a zirconium to magnesium content, expressed as oxides, of about 30:1 to 1:1. The examples of this patent do not disclose any compositions containing aluminum or calcium, although a Zr-Mg salt of the patent was tested against aluminum chlorhydrate and an Al-Zr-gly salt.

In U.S. Pat. No. 4,017,599 there are disclosed aluminum-zirconium antiperspirant complexes buffered with salts of amino acids including hydroxy aluminum glycinates and alkaline and alkaline earth glycinates. This patent suggests that the various alkaline salts, including sodium, potassium, ammonium, magnesium and calcium, are equally suitable. Example V of this patent describes a solid aluminum-zirconium hydroxybromide composition containing 2.24% Al, 31.2% Zr, 28.6% Br, 4.26% glycine, and 1.10% Ca. This composition thus appears to contain about 82% (USP) of non-enhanced active (i.e. Al-Zr-OH-Br with Al:Zr=0.25:1 (mole ratio)) with a Ca:Al+Zr weight ratio of about 1:30.4 and a glycine:Al+Zr weight ratio of about 1:7.8. The extremely low Al:Zr ratio of this salt places it well outside the current FDA monograph.

In CA 1,068,215 there is disclosed a high pay-off antiperspirant stick comprising 5–20% magnesium stearate, 1–5% calcium carbonate, 0–1% mineral oil, 0.1–5% glycine, 0.01–1% deodorant agent, 20–77.8% aluminum chlorhydroxide, 1–10% kaolin, 10–40% rice starch, 0–3% water, and 0.001–1% perfume. The antiperspirant stick is made by making a first blend of the aluminum salt with mineral oil, making a second blend of the rice starch and water, making a third blend of the remaining ingredients, then mixing the three blends and compressing the mixture into a stick.

In WO 96/19228 there are described topical compositions which contain a topical vehicle, a skin irritating ingredient and an anti-irritant amount of an aqueous soluble divalent calcium cation in an amount of 10 mM to 3000 mM. This publication generally suggests a wide variety of topical compositions including sunscreens, insect repellants, shave creams, depilatories, shampoos, permanent wave and hair straightener products, detergents, drug products, antiperspirant and deodorant products, lozenges, mouthwashes, suppositories, etc.

In U.S. Pat. No. 5,534,246 there are disclosed clear water-in-oil antiperspirant emulsions in which the refractive indices of the oil and water phases are matched. A variety of refractive index adjusting compounds are disclosed, one of which is calcium chloride. Examples 5 and 6 disclose aqueous solutions containing, respectively, 32.94% and 36.25% aluminum chlorhydrate and 11.94% and 6.88% calcium chloride.

In U.S. Pat. No. 5,676,936 there are disclosed alcohol based antiperspirant compositions in which the antiperspirant salt is suspended in an alcohol carrier. Prior to addition of the antiperspirant salt, an anti-dissolution agent is incorporated into the alcohol to inhibit dissolution of the antiperspirant salt in the alcohol. The anti-dissolution agent may be a compound having a basic nitrogen function or a basic oxygen function. Compounds having a basic nitrogen function include amino acids. Compounds having a basic oxygen function include inorganic bases such as sodium, potassium, lithium, calcium and magnesium hydroxide.

Michniak, Int'l. J. Cosm. Sci. 3, 29–36 (1981), describes the effect of various polyvalent cations on sweat production using a rat foot pad test. Calcium chloride solution was found to promote sweating. Calcium chloride was also found to reduce the effectiveness of aluminum, lanthanum and zirconium solutions.

It would be highly desirable to provide enhanced efficacy antiperspirant salts which are stable in aqueous solution. This would make it possible to use the enhanced salts in finished formulations that require a soluble salt form, such as the currently attractive clear gel compositions which have been successfully introduced in recent years. It would also be highly desirable to provide a method of making enhanced efficacy antiperspirant salts in concentrated solution—i.e. at salt concentrations greater than 20%. Such a method would be more efficient than current methods, which generally require dilute solutions, thus necessitating removal of large amounts water to obtain the powdered salts.

SUMMARY OF THE INVENTION

The present invention embraces enhanced efficacy antiperspirant salt compositions containing calcium and an amino acid or a hydroxy acid, methods of making such enhanced efficacy antiperspirant salt compositions, stabilized aqueous solutions of such enhanced efficacy antiperspirant salt compositions, and topical compositions containing such enhanced efficacy antiperspirant salt compositions.

A composition in accordance with the present invention comprises, in percent by weight, about 5% to about 78% (USP) of an enhanced efficacy aluminum or aluminum-zirconium antiperspirant salt, about 1% to about 85% water, an amino acid or a hydroxy acid in an amount to provide an (amino or hydroxy) acid:Al+Zr weight ratio of about 2:1 to about 1:20, preferably about 1:1 to about 1:10, and a soluble calcium salt in an amount to provide a Ca:Al+Zr weight ratio of about 1:1 to about 1:28, preferably about 1:2 to about 1:25. Preferred solid antiperspirant salt compositions will comprise about 48% to about 78% (USP), preferably about 66% to about 75%, of an enhanced efficacy aluminum or aluminum-zirconium antiperspirant salt and about 1% to about 16%, preferably about 4 to 13%, bound water along with the aforementioned amount of calcium salt and amino acid or hydroxy acid. Preferred aqueous liquid compositions will comprise about 18% to about 45% (USP), preferably about 20% to about 42%, antiperspirant salt and about 20% to about 80%, preferably about 25% to about 75%, water along with the aforementioned amount of calcium salt and amino acid or hydroxy acid. The HPLC peak 4 to peak 3 area ratio of the antiperspirant salt in these compositions does not degrade as quickly or to as low a point as similar compositions without the calcium salt and amino acid or hydroxy acid. The present invention also embraces a topical composition comprising a dermatologically acceptable vehicle and an antiperspirant effective amount of a stabilized enhanced antiperspirant salt composition as described above.

One method of the present invention involves stabilizing an aqueous solution of an enhanced efficacy aluminum or aluminum-zirconium antiperspirant salt against rapid degradation of the HPLC peak 4 to peak 3 area ratio of said salt by adding to said aqueous antiperspirant salt solution an effective amount of a soluble calcium salt and a water soluble amino acid or hydroxy acid to form a stabilized aqueous enhanced antiperspirant salt solution. A second disclosed method involves preparing an enhanced efficacy aluminum or aluminum-zirconium antiperspirant salt by heating an aqueous solution of an aluminum or an aluminum-zirconium antiperspirant salt in the presence of a soluble calcium salt and a water soluble amino acid or hydroxy acid at a temperature and for a time sufficient to convert the salt to an enhanced antiperspirant salt.

A third disclosed method is an improvement in the method of making an aluminum hydroxy halide or an aluminum hydroxy nitrate by reacting aluminum with an aqueous solution of aluminum halide or aluminum nitrate (or with aqueous hydrogen halide or nitric acid), wherein the improvement comprises including a soluble calcium salt and a water soluble amino acid or hydroxy acid in the reaction mixture. This method provides an aqueous solution of an aluminum antiperspirant salt of the formula $Al_2(OH)_{6-a}X_a$ wherein X is Cl, Br, I or $NO_3$ and a is about 0.3 to about 5 by reacting aluminum with an aqueous solution of $AlX_3$ or HX, wherein the amount of aluminum, the amount of $AlX_3$ or HX, and the time and temperature of reaction are selected so as to provide said antiperspirant salt of the formula $Al_2(OH)_{6-a}X_a$ at a concentration of about 5% to about 45% (USP) by weight, and wherein said aqueous solution of $AlX_3$ or HX additionally comprises a soluble calcium salt and a water soluble amino acid or hydroxy acid in the reaction mixture in an amount to provide a Ca:Al weight ratio of about 1:1 to about 1:28 and an acid:Al weight ratio of about 2:1 to about 1:20.

A fourth method of the present invention involves the preparation of an enhanced aluminum-zirconium antiperspirant salt by the addition of a zirconium antiperspirant salt to an aqueous solution of an enhanced aluminum antiperspirant salt prepared by one of the above-described methods, wherein the amount of zirconium antiperspirant salt is such as to provide an Al:Zr ratio of about 2:1 to about 10:1.

DETAILED DESCRIPTION OF THE INVENTION

Preferred aluminum salts are those having the general formula $Al_2(OH)_{6-a}X_a$ wherein X is Cl, Br, I or $NO_3$, and a is about 0.3 to about 5, preferably about 0.8 to about 2.5, more preferably about 1 to about 2 (such that the Al to X mole ratio is about 0.9:1 to about 2.1:1). These salts generally have some water of hydration associated with them, typically on the order of 1 to 6 moles per mole of salt. Most preferably, the aluminum salt is aluminum chlorohydrate (i.e. X is Cl in the above formula), especially 5/6 basic aluminum chlorohydrate where a is about 1, such that the aluminum to chlorine mole ratio is about 1.9:1 to 2.1:1. Aluminum chlorohydrate is referred to as "ACH" herein.

Preferred aluminum-zirconium salts are mixtures or complexes of the above-described aluminum salts with zirconium salts of the formula $ZrO(OH)_{2-pb}Y_b$ wherein Y is Cl, Br, I, $NO_3$, or $SO_4$, b is about 0.8 to 2, and p is the valence of Y. The zirconium salts also generally have some water of hydration associated with them, typically on the order of 1 to 7 moles per mole of salt. Preferably the zirconium salt is zirconyl hydroxychloride of the formula $ZrO(OH)_{2-b}Cl_b$ wherein b is about 0.8 to 2, preferably about 1.0 to about 1.9. The aluminum-zirconium salts encompassed by the present invention have an Al:Zr mole ratio of about 2 to about 10, and a metal:X+Y ratio of about 0.73 to about 2.1, preferably about 0.9 to 1.5. A preferred salt is aluminum-zirconium chlorohydrate (i.e. X and Y are Cl), which has an Al:Zr ratio of about 2 to about 10 and a metal:Cl ratio of about 0.9 to about 2.1. Thus, the term aluminum-zirconium chlorohydrate is intended to include the tri-, tetra-, penta- and octa-chlorohydrate forms. Aluminum-zirconium chlorohydrate is referred to as "ACH/ZHC" or as "AZCH" herein.

The aluminum and aluminum-zirconium salts of the present invention are of the enhanced efficacy type. By "enhanced efficacy salts" is meant antiperspirant salts which, when reconstituted as 10% aqueous solutions (or if already a solution, diluted with water to about 10% salt concentration in solution), produce an HPLC chromatogram (as described, for example, in U.S. Pat. No. 5,330,751, which is incorporated herein by reference) wherein at least 70%, preferably at least 80%, of the aluminum is contained in two successive peaks, conveniently labeled peaks 3 and 4, and wherein the ratio of the area under peak 4 to the area under peak 3 is at least 0.5, preferably at least 0.7, and more preferably at least 0.9 or higher. Most preferred are salts which exhibit an HPLC peak 4 to peak 3 area ratio of at least 0.7 when measured within two hours of preparation, and which retain a peak 4 to peak 3 area ratio of at least 0.5, preferably at least 0.7, when stored as an aqueous solution of at least 20% salt concentration for one month. Especially preferred are salts wherein at least 30%, more preferably at least 40%, of the aluminum is contained in peak 4. The aluminum present in peaks 3 and 4 should be of the $Al^c$ type, not $Al^b$, when analyzed by the ferron test. Enhanced efficacy aluminum chlorohydrate is referred to as "ACH" herein. Enhanced efficacy aluminum-zirconium chlorohydrate is referred to as "ACH'/ZHC" or as "AZCH'" herein.

The enhanced antiperspirant salts of the present invention have a distinct advantage over previously known enhanced antiperspirant salts in that they will maintain their enhanced state (i.e. they will maintain an elevated peak 4 to peak 3 ratio) in aqueous solution (i.e. solutions containing more than 18% water, typically 20% to 85% water), even at relatively high salt concentrations—for example, at salt concentrations of 18% to 45% (USP) by weight.

The compositions of the present invention include soluble calcium salts. By soluble is meant those calcium salts which are soluble in water or which dissolve in the aqueous solution of antiperspirant salt (i.e. a solution of the aluminum salt and/or zirconium salt). Calcium salts which may be utilized are any of those which do not otherwise interfere with the solubility or effectiveness of the antiperspirant salt. Preferred calcium salts include calcium chloride, calcium bromide, calcium nitrate, calcium citrate, calcium formate, calcium acetate, calcium gluconate, calcium ascorbate, calcium lactate, calcium glycinate and mixtures thereof. Calcium carbonate, calcium sulfate and calcium hydroxide may also be used because they will dissolve in an aqueous solution of the antiperspirant salt. The amount of calcium salt utilized should be that amount which provides a Ca:Al+Zr weight ratio of about 1:1 to about 1:28, preferably about 1:2 to about 1:25. Generally, the aqueous antiperspirant solution will contain about 0.3 to about 3% by weight Ca, preferably about 0.5 to about 2.5% by weight Ca, most preferably about 1.0 to about 2.0% by weight Ca, based on the weight of the entire composition. These amounts of calcium in the final composition may be obtained by the inclusion of about 1% to about 7% by weight of calcium chloride, nitrate or sulfate or similar salts.

The compositions of the present invention also contain a water soluble amino and/or hydroxy acid which is effective in increasing and/or stabilizing the HPLC peak 4:3 area ratio of the antiperspirant salt. Such acids include amino- and/or hydroxy-substituted lower alkanoic acids (including substituted derivatives thereof), preferably where the amino or hydroxy group is located on the α-carbon (i.e. the same carbon to which the carboxy group is attached). The lower alkanoic acid will generally have 2 to 6, preferably 2 to 4, carbon atoms in the alkanoic acid chain. Typical amino and/or hydroxy substituted lower alkanoic acids include any of the amino acids such as glycine, alanine, valine, leucine, isoleucine, P-alanine, serine, cysteine, β-amino-n-butyric acid, γ-amino-n-butyric acid, etc. and hydroxy acids such as glycolic acid and lactic acid. These amino and/or hydroxy substituted lower alkanoic acids may also contain various substituents which do not adversely affect their activity. The preferred amino and/or hydroxy substituted lower alkanoic acids are glycine, alanine, and glycolic acid, with glycine being most preferred. The amount of amino acid or hydroxy acid utilized should be that amount which provides an acid:Al+Zr ratio of about 2:1 to about 1:20, preferably about 1:1 to about 1:10, and most preferably about 1:2 to about 1:7. Generally, the aqueous antiperspirant solution will contain about 1% to about 15% by weight amino acid or hydroxy acid, preferably about 2% to about 10% by weight, based on the weight of the entire composition. The amino and/or hydroxy acid need not be separately added to the composition, but may be included as part of the antiperspirant salt complex such as, for example, Al-Zr-Gly salts (e.g. aluminum-zirconium tetrachlorohydrate-gly). The glycine content of such salts may be adjusted to provide the aforementioned ratio. The amino and/or hydroxy acid may also be added as a salt, particularly the calcium salt such as, for example, calcium glycinate.

Stabilization of enhanced antiperspirant salt solutions with calcium and amino or hydroxy acid.

One aspect of the present invention involves the preparation of stabilized aqueous solutions of enhanced efficacy antiperspirant salts by the inclusion of calcium and an amino acid or hydroxy acid. That is, an aqueous solution of an enhanced antiperspirant salt, which would ordinarily lose 4:3 peak ratio rapidly, particularly at higher concentrations, may be stabilized by the inclusion of calcium and an amino acid or hydroxy acid in the solution. By "stabilized" is meant that the peak 4 to peak 3 ratio, while it may degrade somewhat, will not degrade as quickly or to as low a point as an unstabilized salt (i.e. salt solution without calcium and amino acid present). That is, the peak 4 to peak 3 ratio (HPLC area) will remain at 0.5 or higher, preferably at least 0.7, for at least one month at room temperature. To achieve stabilization the composition will comprise in percent by weight (USP) about 18% to about 45%, preferably about 20% to about 42%, antiperspirant salt, about 20% to about 80%, preferably about 25% to about 70%, water, an amino acid or a hydroxy acid in an amount to provide an acid:Al+Zr weight ratio of about 2:1 to about 1:20, preferably about 1:1 to about 1:10, and a soluble calcium salt in an amount to provide a Ca:Al+Zr weight ratio of about 1:1 to about 1:28, preferably about 1:2 to about 1:25. This aspect of the invention may be demonstrated by Examples 1 and 2 below.

EXAMPLE 1

An aqueous solution containing 20% or 30% (USP) enhanced aluminum-zirconium tetrachlorohydrate-gly (Al:Zr=3.6 (mole ratio); Gly:Al+Zr=1:2.5 (wt. ratio)) was prepared by dissolving an appropriate amount of the powdered enhanced salt in water to provide the concentration indicated in Tables 1A and 1B below. The powdered salt had been previously prepared by heating an approximately 10% aqueous solution of ACH at about 85° C. for about 16 to 20 hours, adding ZHC-gly, then spray drying. To this solution was also added an amount of calcium chloride dihydrate (or calcium sulfate or nitrate where indicated) to provide the concentration of Ca and the Ca:Al+Zr weight ratio indicated in the Tables. The HPLC peak 4 to peak 3 area ratio is also given in the Tables for one month or two weeks after preparation.

TABLE 1A

Stability of 4/3 Ratio of Aqueous 20% Enhanced Al—Zr-Gly With Calcium

| Al—Zr % (USP) | 20% | 20% | 20% | 20% | 20% | 20% | 20% | 20% |
|---|---|---|---|---|---|---|---|---|
| Ca % | 0% | 0.3% | 0% | 0.5% | 1.0% | 1.5% | 2.0% | 2.5% |
| Ca: Al + Zr 4/3 ratio, | 0 | 1:25 | 0 | 1:15 | 1:7.5 | 1:5 | 1:3.8 | 1:3 |
| t = 0 | 1.51 |  | 1.67 |  |  |  |  |  |
| t = 1 mo | 0.31 | 1.26 | 0.35 | 1.86 | 2.57 | 2.96 | 3.16 | 3.12 |

As will be seen from the above data, the addition of 0.3 to 2.5% calcium to a 20% aqueous aluminum-zirconium tetrachlorohydrate-gly solution (Gly:Al+Zr=1:2.5) stabilizes the 4:3 peak ratio at a high level (i.e. >0.9), whereas the solutions without calcium drop below 0.5. Generally, peak ratio increases as calcium level increases. When similar solutions were tested with calcium replaced by magnesium, tin, zinc, and barium, the 4:3 peak ratio was not stabilized.

TABLE 1B

Stability of 4/3 Ratio of Aqueous 30% Enhanced Al—Zr-Gly With Calcium

| Al—Zr % (USP) | 30% | 30% | 30% | 30% | 30% | 30% | 30% |
|---|---|---|---|---|---|---|---|
| Ca % | 0% | 0.6% | 1.1% | 1.6% | 1% (Cl$_2$) | 1% (SO$_4$) | 1% (NO$_3$) |
| Ca: Al + Zr 4/3 ratio, | 0 | 1:19 | 1:11 | 1:7 | 1:12 | 1:12 | 1:12 |
| t = 0 | 1.51 |  |  |  |  |  |  |
| t = 2 wks |  |  |  |  | 2.24 | 1.64 | 2.31 |
| t = 1 mo | 0.10 | 1.17 | 1.58 | 1.84 |  |  |  |

As will be seen from the above data, the addition of 0.6 to 1.6% calcium to a 30% aqueous aluminum-zirconium tetrachlorohydrate-gly solution stabilizes the 4:3 peak ratio at a high level (i.e. >0.9), whereas the solutions without calcium drop below 0.5. This stabilizing effect is also shown for the sulfate and nitrate salts of calcium in addition to the chloride salt.

EXAMPLE 2

Aqueous solutions containing 25% (USP) enhanced aluminum chlorohydrate were prepared by dissolving an appropriate amount of the powdered enhanced salt in water. The powdered salt had been previously prepared by heating an approximately 10% aqueous solution of ACH at about 85° C. for about 16 to 20 hours, then spray drying. To each of these solutions was also added an amount of calcium chloride dihydrate and glycine (or alanine or glycolic acid) to provide the concentration of Ca and glycine (or alanine or glycolic acid) indicated in Tables 2A and 2B. The Ca:Al weight ratio and the Gly (or acid):Al weight ratio for each solution are also given in Tables 2A and 2B as is the HPLC peak 4 to peak 3 area ratio after one day storage.

TABLE 2A

Stability of 4/3 Ratio of Aqueous 25% ACH' With Calcium And Glycine

| ACH % (USP) | 25% | 25% | 25% | 25% | 25% | 25% | 25% | 25% |
|---|---|---|---|---|---|---|---|---|
| Ca % | 0% | 0.5% | 2.5% | 0% | 1.0% | 1.5% | 2.0% | 1.0% |
| Gly % | 0% | 0% | 0% | 4% | 4% | 4% | 4% | 2% |

TABLE 2A-continued

Stability of 4/3 Ratio of Aqueous 25%
ACH' With Calcium And Glycine

| Ca: Al | 0 | 1:15 | 1:3 | 0 | 1:7.5 | 1:5 | 1:3.8 | 1:7.5 |
|---|---|---|---|---|---|---|---|---|
| Gly: Al | 0 | 0 | 0 | 1:1.9 | 1:1.9 | 1:1.9 | 1:1.9 | 1:3.8 |
| 4/3 ratio, | | | | | | | | |
| t = 0 | 0.72 | | | | | | | |
| t = 1 day | 0.36 | 0.32 | 0.38 | 0.26 | 0.95 | 0.96 | 1.01 | 0.68 |

As will be seen from the above data, the addition of calcium alone or glycine alone to a 25% aqueous enhanced aluminum chlorohydrate solution does not stabilize the 4:3 peak ratio. Both calcium and glycine must be present to stabilize the 4:3 peak ratio at a high level (i.e. >0.5). Generally, peak ratio increases as calcium level increases and as glycine level increases. However, little benefit is obtained with calcium levels greater than 2.5% and glycine levels greater than 6%.

TABLE 2B

Stability of 4/3 Ratio of Aqueous 25%
ACH' With Calcium & Alanine/Glycolic Acid

| ACH % (USP) | 25% | 25% | 25% | 25% | 25% | 25% | 25% | 25% |
|---|---|---|---|---|---|---|---|---|
| Ca % | 1.0% | 1.0% | 1.0%, | 1.0% | 1.0% | 1.0% | 1.0% | 1.0% |
| Alanine % | 0% | 2% | 4% | 6% | | | | |
| Glycolic Acid % | | | | | 0% | 2% | 4% | 6% |
| Ala or GA: Al | 0 | 1:3.8 | 1:1.9 | 1:1.3 | 0 | 1:3.8 | 1:1.9 | 1:1.3 |
| 4/3 ratio, | | | | | | | | |
| t = 0 | 0.72 | | | | | | | |
| t = 1 day | 0.40 | 0.96 | 1.43 | 1.53 | 0.45 | 0.47 | 0.85 | 0.98 |

As will be seen from the above data, the addition of 1% calcium alone to a 25% aqueous enhanced aluminum chlorohydrate solution does not stabilize the 4:3 peak ratio. However, the addition of alanine (2% to 6%) or glycolic acid (4% to 6%), in place of glycine, along with 1% calcium is shown to stabilize the 4:3 peak ratio at a high level (i.e. >0.5). Generally, peak ratio increases as calcium level increases and as amino acid or hydroxy acid level increases. In a further experiment, it was determined that the addition of 4% leucine, isoleucine, β-alanine, cysteine, valine, serine, β-amino-n-butyric acid and γ-amino-n-butyric acid to a 25% aluminum chlorohydrate solution containing 1% calcium also stabilized the 4:3 peak ratio at a high level (i.e. >0.5).

The calcium and glycine need not be added separately to the antiperspirant salt solution, but may be advantageously added together as calcium glycinate. As a further example, an aqueous calcium glycinate slurry (made by heating calcium carbonate with glycine in water) was added to an aqueous solution of enhanced aluminum chlorohydrate to form a solution containing 25% (USP) ACH', 1% Ca and 2% glycinate. After one week the salt solution had an HPLC peak 4:3 area ratio of 0.63, confirming the peak stabilizing effect of the calcium glycinate.

Powdered enhanced antiperspirant salts containing calcium and amino or hydroxy acid with high and stable HPLC peak 4:3 area ratio.

Powdered enhanced antiperspirant salts with high and stable peak 4:3 ratios may be prepared by spray drying the aforedescribed solutions of such salts containing calcium and an amino acid. This will produce powdered salts containing about 48% to about 78%, preferably about 66% to about 75%, antiperspirant salt (preferably aluminum-zirconium chlorohydrate), an amino acid or a hydroxy acid (preferably glycine or alanine) in an amount to provide an acid:Al+Zr weight ratio of about 1:1 to about 1:10 (generally, about 5% to about 18% amino acid by weight of the powdered composition), and a soluble calcium salt in an amount to provide a Ca:Al+Zr weight ratio of about 1:1 to about 1:28, preferably about 1:2 to about 1:25 (generally, about 1% to about 10% calcium by weight of the powdered composition). Such powdered salts will also contain some water of hydration, typically about 1% to about 16%, preferably about 4 to 13%, by weight.

EXAMPLE 3

An aqueous solution containing 20% (USP) enhanced aluminum-zirconium tetrachlorohydrate-gly (Al:Zr=3.6 (mole ratio); Gly:Al+Zr=1:2.5 (weight ratio)) was prepared by dissolving an appropriate amount of the powdered enhanced salt in water. The powdered salt had been previously prepared by heating an approximately 10% aqueous solution of ACH at about 85° C. for about 16 to 20 hours, adding ZHC-gly, then spray drying. To three different portions of this solution was also added an amount of calcium chloride dihydrate to provide solutions containing respectively 1%, 2% and 3% Ca (Ca:Al+Zr=1:7.5, 1:3.8 and 1:2.5). These solutions were allowed to stand for three weeks and then spray dried to provide powdered salts having the composition and HPLC peak 4 to peak 3 area ratio shown in Table 3.

TABLE 3

Powdered Enhanced Al—Zr—Gly Containing Calcium

| Al—Zr % (USP) | ~64% | ~57% | ~52% |
|---|---|---|---|
| Ca % | 3.3% | 5.6% | 7.7% |
| Gly % | ~9% | ~8% | ~7% |
| H$_2$O | 11.9% | 12.6% | 11.7% |
| 4/3 ratio | 3.27 | 3.77 | 3.88 |

Aging non-enhanced antiperspirant salt solutions in the presence of calcium and amino or hydroxy acid to form enhanced antiperspirant salt solutions.

A further aspect of the present invention involves heat treating (or aging) aqueous solutions of non-enhanced antiperspirant salts in the presence of a soluble calcium salt and an amino and/or hydroxy acid to form solutions of enhanced antiperspirant salts. While conventional heat treating generally requires relatively low concentrations of the non-enhanced antiperspirant salt, the present process, which includes calcium and an amino and/or hydroxy acid, may be performed with relatively high concentrations of the antiperspirant salt (e.g. 18% to 45% USP), thus avoiding the need to remove large quantities of water associated with dilute solutions. The concentrated solution of the enhanced antiperspirant salt may then be used directly in finished formulations which utilize an aqueous antiperspirant salt (such as in clear gels or aqueous roll-ons) or it may be spray dried or vacuum dried to a powder.

The conversion of aqueous antiperspirant salt (e.g. aluminum chlorohydrate or aluminum-zirconium chlorohydrate) to aqueous enhanced antiperspirant salt is performed by aging the solution at a temperature (typically about 40° to about 100° C.) and for a time (typically about 2 to about 120 hours) sufficient to convert the aluminum salt to enhanced efficacy form (i.e. HPLC peak 4 to peak 3 area ratio greater than 0.5, preferably greater than 0.7). The aqueous aluminum salt concentration is generally at about 18% to about 45% (USP), preferably about 20% to about 42% (USP), during the heat treatment conversion. The amount of calcium salt and the amount of amino and/or hydroxy acid will each be an effective amount to increase and/or stabilize the HPLC peak 4:3 area ratio of the salt The amount of amino and/or hydroxy acid (preferably glycine or alanine) will be an amount to provide an acid:Al+Zr weight ratio of about 2:1 to about 1:20, preferably about 1:1 to about 1:10 (generally, about 2% to about 9% by weight of the solution), and the amount of soluble calcium salt will be an amount to provide a Ca:Al+Zr weight ratio of about 1:1 to about 1:28, preferably about 1:2 to about 1:25 (generally, about 0.3% to about 3% by weight of the solution). The solution of enhanced antiperspirant salt produced will have a stabilized peak 4 to peak 3 ratio. The conversion to the enhanced salt may be conducted at room temperature (about 25° C.), but this may require up to about two weeks of aging. The conversion may also be performed more quickly with microwave heating.

EXAMPLE 4

Aqueous solutions containing about 37% (USP) non-enhanced aluminum-zirconium tetrachlorohydrate-gly (Al:Zr=3.6 (mole ratio); Gly:Al+Zr=1:2.5 (wt. ratio); peak 4:3=<0.2) and 1% calcium (added as calcium chloride dihydrate) were aged at the temperatures and for the times shown in Table 4 to provide solutions of enhanced salts. Similarly, an aqueous solution (50 g) containing about 30% non-enhanced aluminum-zirconium tetrachlorohydrate-gly (Al:Zr=3.6; Gly:Al+Zr=1:2.5; peak 4:3=<0.2) and 2% calcium was heated in a CEM AVC80 microwave oven at 100% power (630 watts) for two minutes. The HPLC peak 4 to peak 3 area ratio of each converted salt is also shown in Table 4.

TABLE 4

Conversion of Aqueous 37% & 30% Al—Zr—Gly With Calcium To Enhanced Salt

| Al—Zr % (USP) | 37% | 37% | 37% | 37% | 30% |
|---|---|---|---|---|---|
| Ca % | 1% | 1% | 1% | 1% | 2% |
| Ca:Al + Zr | 1:14 | 1:14 | 1:14 | 1:14 | 1:6 |
| Temp. | 85° C. | 60° C. | 45° C. | 25° C. | microwave |
| Time | 6 hr | 14 hr | 120 hr | 264 hr | 2 min |
| 4/3 ratio | 0.65 | 0.79 | 0.97 | 0.60 | 0.70 |

EXAMPLE 5

Standard 50% (~41% USP) aluminum chlorohydrate (ACH) solution (non-enhanced) was diluted with water to form several solutions of about 33% USP salt concentration and varying amounts of glycine and calcium chloride dihydrate were added to these solutions to provide the concentration of Ca and glycine shown in Table 5. Each solution was then heated at 85° C. for 16 hours. For each treated solution, the HPLC peak 4 to peak 3 area ratio and the percentage of peak 4 aluminum is also shown in Table 5.

TABLE 5

Conversion Of Aqueous 33% ACH To ACH' With Calcium And Glycine

| ACH % (USP) | 33% | 33% | 33% | 33% | 33% | 33% | 33% |
|---|---|---|---|---|---|---|---|
| Ca % | 0 | 1% | 1.5% | 2% | 2% | 2% | 2% |
| Gly % | 4% | 4% | 4% | 4% | 0% | 2% | 6% |
| Ca: Al | 0 | 1:10 | 1:6.7 | 1:5 | 1:5 | 1:5 | 1:5 |

TABLE 5-continued

Conversion Of Aqueous 33% ACH To ACH' With Calcium And Glycine

| Gly: Al | 1:2.5 | 1:2.5 | 1:2.5 | 1:2.5 | 0 | 1:5 | 1:1.7 |
|---|---|---|---|---|---|---|---|
| 4/3 ratio | 0.12 | 1.38 | 1.71 | 1.95 | 0.00 | 0.73 | 4.07 |
| Peak 4% | 7.96 | 41.81 | 52.67 | 58.38 | 0.00 | 30.21 | 63.84 |

From the above data, it can be seen that heat treatment of 33% ACH will convert the salt to enhanced form, as evidenced by peak 4 to peak 3 area ratio greater than 0.5, when both calcium and amino acid are present in the solution. However, such a concentrated ACH solution will not convert to enhanced form when either calcium or amino acid are not present. It can be seen that the peak 4 content of the enhanced salt increases with increasing Ca and with increasing Glycine, the lowest amount of peak 4 being 30% at a glycine level of 2%.

Reaction of Al with $AlX_3$ or HX in the Presence of calcium and amino or hydroxy acid.

A further aspect of the present invention involves the reaction of aluminum (Al) with aluminum halide or aluminum nitrate ($AlX_3$), typically $AlCl_3$, or with hydrogen halide or nitric acid (HX), typically HCl, to form the aluminum halohydrate (hydroxyhalide) or aluminum hydroxy nitrate ($Al_2(OH)_{6-a}X_a$), typically aluminum chlorohydrate (ACH). This reaction is well-known and is the method generally utilized to prepare conventional, non-enhanced 50% (~41% USP) ACH solutions on a commercial basis. It has been suggested that enhanced aluminum chlorohydrate (ACH') can be prepared directly by this reaction if the reactants are mixed at a relatively dilute concentration so that the final concentration of ACH' in the solution is below 20%, preferably about 10%. In this regard see, for example, U.S. Pat. No. 4,859,446, U.S. Pat. No. 4,944,933, and U.S. Pat. No. 5,356,609. This direct synthesis of ACH' has little or no advantage over the known heat treatment of dilute ACH to form ACH' since dilute solutions are still required, making it necessary to remove large quantities of water to obtain the desired product in powder form, the only form in which the product is stable. In addition, this direct synthesis suffers from the significant disadvantage in that a substantial amount of $Al^b$ is produced, typically about 20 to 60% of the total aluminum. This is in contrast to the 2 to 5% $Al^b$ produced in the conventional heat treatment of ACH to form ACH'. This $Al^b$, which does not provide enhanced efficacy, also appears in peak 4 along with the enhanced $Al^{c'}$.

In accordance with the present invention, it was discovered that if the reaction of aluminum with aluminum halide (or hydrogen halide) or with aluminum nitrate (or nitric acid) is performed in the presence of calcium and an amino acid (or a hydroxy acid), enhanced aluminum halohydrate or aluminum hydroxy nitrate is preferentially formed even at relatively high concentrations (i.e. at concentrations greater than 20%). These concentrated solutions have an initial HPLC peak 4 to 3 area ratio greater than 0.5, preferably greater than 0.7, and most preferably greater than 0.9. In addition, the peak ratio is stabilized in an enhanced state (i.e. the peak ratio remains greater than 0.5) for at least one month in aqueous solution.

The above-described reaction may be carried out within the following parameters. The amount of aluminum and aluminum halide (or aluminum nitrate or hydrogen halide or nitric acid) added will be an approximately stoichiometric amount (although a slight excess of aluminum may be desired) so as to provide about a 5% to about a 45% (USP) solution, preferably about a 20% to 42% (USP) solution, of the enhanced aluminum halohydrate (or aluminum hydroxy nitrate) desired. Concentrations above 20% are preferred for economic efficiency. The amount of amino acid (preferably glycine or alanine) or hydroxy acid should be sufficient to provide an acid:Al weight ratio of about 1:1 to about 1:10 (i.e. typically about 1% to about 12% by weight of the final solution). The amount of calcium salt should be sufficient to provide a Ca:Al weight ratio of about 1:1 to about 1:28, preferably about 1:2 to about 1:25 (i.e. typically about 0.3% to about 3% by weight of the final solution). The temperature of the reaction may be from about 50° C. to about 120° C., preferably about 80° to 105° C., and the reaction time may vary, depending on the reaction temperature, from about 1 to 100 hours, preferably about 3 to 12 hours, most preferably about 4 to 6 hours. Generally, the reaction will be carried out until the desired aluminum to halide (or nitrate) ratio is achieved (broadly 0.8 to 2.5, and typically 1.9 to 2.1 for 5/6 ACH').

EXAMPLE 6

Three solutions of about 32% (USP) ACH were prepared by reacting, at 100° C. for 5 hours in a flask fitted with a condenser, 26 g Al with 234 g aqueous HCl (~7.9%). The second solution also contained 9.6 g calcium chloride dihydrate and the third solution contained 9.6 g calcium chloride dihydrate and 10.4 g glycine. The HPLC peak 4 to peak 3 area ratio for the first two solutions was less than 0.2, while that of the third solution, which contained both calcium and glycine, was about 1.1.

Preparation of enhanced aluminum-zirconium aqueous solutions from enhanced aluminum solutions and powdered salts therefrom.

In accordance with the present invention, enhanced Al-Zr antiperspirant salts may be prepared by adding to an aqueous solution of the enhanced aluminum salt made as described previously (e.g. as described in Ex. 5 or Ex. 6), an amount of zirconium salt (e.g. zirconyl hydroxychloride) sufficient to provide the desired Al:Zr ratio (typically between 2 and 10). In this way aqueous solutions of enhanced Al-Zr salts such as enhanced aluminum-zirconium chlorohydrate may be prepared, advantageously at relatively high concentration (i.e. 18–45% USP). These solutions may also be dried, such as by spray drying or vacuum drying, to provide the enhanced Al-Zr salts in solid (i.e. powder) form.

EXAMPLE 7

About 50 g of the ACH'-Ca-gly solution described in Example 6 was mixed with 29 g of aqueous zirconyl hydroxychloride (ZHC) (16.6% Zr) to provide a concentrated solution of enhanced efficacy aluminum-zirconium tetrachlorohydrate (~32% USP) with an Al/Zr mole ratio of about 3.6 and an HPLC peak 4:3 area ratio of about 1.1. The solution was vacuum dried to provide the salt in solid powder form with a peak 4:3 area ratio of about 1.

Topical compositions containing stabilized enhanced antiperspirant salts of the present invention.

Any of the aforedescribed stabilized enhanced antiperspirant salts may be formulated into topical compositions such as aerosols, pump sprays, roll-ons, lotions, creams, gels, sticks, etc. In particular, aqueous solutions of these stabilized antiperspirant salts may be directly utilized in oil-in-water and water-in-oil emulsions, such as the currently popular clear gel formulations, or in other aqueous based compositions such as aqueous based roll-ons. The powdered enhanced salts may be formulated into any known type of topical composition which utilizes powdered salts, including, in particular aerosol, liquid roll-on, cream and solid stick formulations in which the powdered salt is suspended in an anhydrous, dermatologically acceptable carrier, particularly a carrier comprising a silicone.

EXAMPLE 8

A clear antiperspirant gel composition comprising the following ingredients, in which all parts and percentages are by weight, was prepared following the procedure outlined below.

| | |
|---|---|
| Water | 43.3 |
| Al—Zr Tetrachlorohydrate-Gly/Ca[1] | 27.7 |
| Propylene Glycol | 1.0 |
| Ethanol | 10.0 |
| Dimethicone (DC-225) | 9.7 |
| Dimethicone Copolyol (DC-3225C) | 8.1 |
| Fragrance | 0.2 |

The above composition was made in the following manner. The water phase components (AZCH'-Ca-gly, propylene glycol, ethanol, water) and the oil phase components are each mixed in separate containers and filtered and the refractive index of each is measured. The refractive index of the water phase is adjusted to match the refractive index of the oil phase to within 0.0004 by addition of water or propylene glycol as required. The water phase is then slowly added to the oil phase at about 18° C. with sufficient mixing to form a clear emulsion with minimum aeration. This emulsion is then sheared to form a clear gel with a viscosity of about 130,000 to 160,000 cP.

After aging at ambient temperature for three months, the product of Example 8 was compared to Gillette® Series Clear Gel Antiperspirant, which has a similar formulation but contains non-enhanced aluminum-zirconium tetrachlorohydrate-gly, the only previously available aqueous form. The two products were tested for thermal efficacy (i.e. hot room sweat reduction) in separate panel studies involving 45 female panelists (AvB; test product applied to one axilla and control product applied to other axilla). The test product (Ex. 8) exhibited a significant improvement in thermal efficacy versus the control.

Throughout the specification reference to HPLC analysis means that chromatograms were obtained as follows: Salt solutions are evaluated for aluminum polymer distribution by HPLC at a concentration of about 10% Al or Al-Zr salt. If the solution to be analyzed is at a higher salt concentration, it is diluted with sufficient water to bring the salt concentration to about 10%. A 1.0 μL sample is pumped through a 4.6 mm×50 cm column packed with Nucleosil 100-5 (Keystone Scientific Inc.) using a 0.01M aqueous nitric acid solution as the eluent. The flow rate of the mobile phase was controlled at 0.5 mL/min with a Waters 100 unit. HPLC profiles were recorded and processed with a computerized system that included the Millennium 2010 Chromatography Manager software from the Millipore/Waters Corp. A Waters 410 differential refractometer was used as the refractive index detector. The HPLC profiles are read from left to right (higher to lower molecular weight). Following this technique, peaks 3 and 4 appear at retention times of Kd=0.32–0.38 and Kd=0.49–0.53 respectively. Naturally, of course, other HPLC techniques which use different column materials, eluents and flow rates can be used provided that they sufficiently resolve peaks 3 and 4 with an acceptable degree of precision (i.e. the technique must be capable of resolving the Al into five distinct peaks). Obviously, such other techniques may place peaks 3 and 4 at different retention times from those given above.

It should be noted that reference throughout this application to weight percent of antiperspirant salt is intended to be calculated as anhydrous weight percent in accordance with the new U.S.P. method. This calculation excludes any bound water and glycine. For aluminum chlorohydrate and aluminum-zirconium chlorohydrate, the calculation is as follows:

$$\%ACH = \%Al[26.98x + 17.01(3x-1) + 35.45]/26.98x \text{ where } x = Al/Cl \text{ ratio;}$$

$$\%AZCH = \%Al\{26.98y + 92.97 + 17.01[3y+4-(y+1)/z] + 35.45(y+1)/z\}/26.98y \text{ where } y = Al/Zr \text{ ratio and } z = metal/Cl \text{ ratio.}$$

For reference purposes, calculation of antiperspirant salt weight percent in accordance with the U.S.P. method compares to the previously used standard industry method as follows: 50% ACH (std.) ≈40.8% (USP); 50% AZCH (std) ≈38.5% USP.

What is claimed is:

1. A stable antiperspirant composition comprising, in percent by weight, about 5% to about 78% (USP) of an enhanced efficacy aluminum or aluminum-zirconium antiperspirant salt having an HPLC peak 4 to peak 3 area ratio of at least 0.5 with at least 70% of the aluminum contained in said peaks 3 and 4, about 1% to about 85% water, a water soluble amino and/or hydroxy acid in an amount to provide an acid:Al+Zr weight ratio of about 2:1 to about 1:20, and a soluble calcium salt in an amount to provide a Ca:Al+Zr weight ratio of about 1:1 to about 1:28.

2. The composition of claim 1 wherein said amino and/or hydroxy acid is an amino- and/or hydroxy-substituted lower alkanoic acid.

3. The composition of claim 2 wherein said calcium salt is selected from the group consisting of calcium chloride, calcium bromide, calcium nitrate, calcium citrate, calcium formate, calcium acetate, calcium gluconate, calcium ascorbate, calcium lactate, calcium glycinate, calcium carbonate, calcium sulfate, calcium hydroxide, and mixtures thereof.

4. The composition of claim 3 wherein said enhanced efficacy antiperspirant salt comprises enhanced efficacy aluminum chlorohydrate or enhanced efficacy aluminum-zirconium chlorohydrate.

5. The composition of claim 1 or 4 wherein said amino and/or hydroxy acid is selected from the group consisting of glycine, alanine, glycolic acid, leucine, isoleucine, β-alanine, cysteine, valine, serine, β-amino-n-butyric acid and γ-amino-n-butyric acid and salts thereof.

6. The composition of claim 4 wherein said amino and/or hydroxy acid comprises glycine.

7. The composition of claim 4 in the form of an aqueous solution comprising about 20% to about 42% (USP) of said enhanced efficacy aluminum or aluminum-zirconium antiperspirant salt and about 25% to about 75% water, wherein said acid:Al+Zr weight ratio is about 1:1 to about 1:10 and said Ca:Al+Zr weight ratio is about 1:2 to about 1:25.

8. The composition of claim 7 wherein said enhanced efficacy antiperspirant salt has an HPLC peak 4 to peak 3 area ratio of at least 0.7 with at least 80% of the aluminum contained in said peaks 3 and 4.

9. The composition of claim 4 in the form of a solid powder comprising about 66% to about 75% (USP) of said enhanced efficacy aluminum or aluminum-zirconium antiperspirant salt and about 4% to about 13% water, wherein said acid:Al+Zr weight ratio is about 1:1 to about 1:10 and said Ca:Al+Zr weight ratio is about 1:2 to about 1:25.

10. The composition of claim 9 wherein said enhanced efficacy antiperspirant salt has an HPLC peak 4 to peak 3 area ratio of at least 0.7 with at least 80% of the aluminum contained in said peaks 3 and 4.

11. The composition of claim 1 comprising about 18% to about 75% (USP) of said enhanced efficacy aluminum or aluminum-zirconium antiperspirant salt and about 4% to about 75% water, wherein said acid:Al+Zr weight ratio is about 1:1 to about 1:10 and said Ca:Al+Zr weight ratio is about 1:2 to about 1:25.

12. The composition of claim 11 wherein said enhanced efficacy antiperspirant salt comprises enhanced efficacy aluminum chlorohydrate or enhanced efficacy aluminum-zirconium chlorohydrate, wherein said enhanced efficacy antiperspirant salt has an HPLC peak 4 to peak 3 area ratio of at least 0.7 with at least 80% of the aluminum contained in said peaks 3 and 4.

13. The composition of claim 12 wherein said amino and/or hydroxy acid is an amino- and/or hydroxy-substituted lower alkanoic acid.

14. The composition of claim 13 wherein said calcium salt is selected from the group consisting of calcium chloride, calcium bromide, calcium nitrate, calcium citrate, calcium formate, calcium acetate, calcium gluconate, calcium ascorbate, calcium lactate, calcium glycinate, calcium carbonate, calcium sulfate, calcium hydroxide, and mixtures thereof.

15. The composition of claim 1 in the form of an aqueous solution comprising about 18% to about 45% (USP) of said enhanced efficacy aluminum or aluminum-zirconium antiperspirant salt and about 20% to about 80% water.

16. The composition of claim 15 wherein said amino and/or hydroxy acid is an amino- and/or hydroxy-substituted lower alkanoic acid.

17. The composition of claim 16 wherein said calcium salt is selected from the group consisting of calcium chloride, calcium bromide, calcium nitrate, calcium citrate, calcium formate, calcium acetate, calcium gluconate, calcium ascorbate, calcium lactate, calcium glycinate, calcium carbonate, calcium sulfate, calcium hydroxide, and mixtures thereof.

18. The composition of claim 1 in the form of a solid powder comprising about 48% to about 78% (USP) of said enhanced efficacy aluminum or aluminum-zirconium antiperspirant salt and about 1% to about 16% water.

19. The composition of claim 18 wherein said amino and/or hydroxy acid is an amino- and/or hydroxy-substituted lower alkanoic acid.

20. The composition of claim 19 wherein said calcium salt is selected from the group consisting of calcium chloride, calcium bromide, calcium nitrate, calcium citrate, calcium formate, calcium acetate, calcium gluconate, calcium ascorbate, calcium lactate, calcium glycinate, calcium carbonate, calcium sulfate, calcium hydroxide, and mixtures thereof.

21. The composition of claim 14, 17 or 20 wherein said amino and/or hydroxy acid is selected from the group consisting of glycine, alanine, glycolic acid, leucine, isoleucine, β-alanine, cysteine, valine, serine, β-amino-n-butyric acid and γ-amino-n-butyric acid and salts thereof.

22. The composition of claim 21 wherein said enhanced efficacy antiperspirant salt comprises enhanced efficacy aluminum chlorohydrate or enhanced efficacy aluminum-zirconium chlorohydrate.

23. The composition of claim 22 wherein said amino and/or hydroxy acid comprises glycine.

24. A topical antiperspirant composition comprising a perspiration reducing effective amount of a composition according to claim 9 or 20 suspended in an anhydrous carrier.

25. A topical antiperspirant composition in the form of an aerosol, pump spray, roll-on, lotion, cream, gel, or stick comprising a perspiration reducing effective amount of a composition according to claim 1, 4, 7 or 9.

26. A clear antiperspirant gel composition comprising a water-in-oil emulsion wherein the water phase comprises a composition according to claim 1, 4, 7 or 9.

27. A method of reducing perspiration from human skin comprising applying to human skin a perspiration reducing effective amount of a composition according to claim 1, 4, 7 or 9.

* * * * *

UNITED STATES PATENT AND TRADEMARK OFFICE
CERTIFICATE OF CORRECTION

PATENT NO. : 6,245,325 B1
DATED : June 12, 2001
INVENTOR(S) : Yan-Fei Shen

It is certified that error appears in the above-identified patent and that said Letters Patent is hereby corrected as shown below:

Column 14,
Line 22, (after the Table), insert the following footnote:
-- [1] Added as 30% (USP) aqueous solution to which was added sufficient $CaCl_2$ dihydrate to provide Ca:Al+Zr = 1:6.2 (2% Ca) and peak 4:3 area ratio = 2. Final gel composition contains 23.3% AZCH' (~18% USP) and 4.4% $CaCl_2$ dihydrate (~1.2% Ca). --

Signed and Sealed this

Twenty-third Day of September, 2003

JAMES E. ROGAN
*Director of the United States Patent and Trademark Office*